US006991930B1

(12) United States Patent
Janisiewicz (10) Patent No.: US 6,991,930 B1
(45) Date of Patent: Jan. 31, 2006

(54) **BIOLOGICAL CONTROL OF POSTHARVEST DECAY OF FRUIT USING STRAINS OF *METSCHNIKOWIA* SPECIES**

(75) Inventor: Wojciech Janisiewicz, Frederick, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 178 days.

(21) Appl. No.: 10/140,817

(22) Filed: May 9, 2002

(51) Int. Cl.
 *C12N 1/14* (2006.01)
 *A01N 63/04* (2006.01)
(52) U.S. Cl. .................................. 435/254.2; 424/93.51
(58) Field of Classification Search ............. 435/255.1;
 424/93.51
 See application file for complete search history.

(56) References Cited

PUBLICATIONS

Janisiewicz et al., Phytopathology (2001), 91(11), 1098-1108.*
Migheli et al. 1997. Ned. Fac. Landbouww. Univ. Gent. vol. 62, pp. 1065-1070.*
Benbow, J., et al., "Fruit Surface Colonization and Biological Control of Postharvest Diseases of Pear by Preharvest. Yeast Applications", *Plant Disease*, vol. 83, (9), pp. 839-844, Sep. 1999.
Chand-Goyal, T., et al., "Control of Postharvest Pear Diseases Using Natural Saprophytic Yeast Colonists and their Combination With a Low Dosage of Thiabendazole", *Postharvest Biology and Technology*, vol. 7, pp. 51-64, 1996.
Chand-Goyal, T., et al., "Biological Control of Postharvest Diseases of Apple and Pear Under Semi-Commerical and Commerical Conditions Using Three Saprophytic Yeasts", *Biological Control*, vol. 10, pp. 199-206, 1997.
Daverport, R.R., "Distribution of Yeasts and Yeast-Like Organisms From Aerial Surfaces of Developing Apples and Grapes", *University of Bristol, Long Ashton Research Station*, Bristol, BS18 9AF, U.K., pp. 323-359.
De Curtis, F., et al., "Selection and Use of *Metschnikowia pulcherrima* as a Biological Control Agent for Postharvest Rots of Peaches and Table Grapes", *Annali di Microbiologia ed Enzimologia*, vol. 46, pp. 45-55, 1996.

Falconi, C.J., et al., "Epiphytic fungi on Apple Leaves and their Value for Control of the Postharvest Pathogens *Botrytis cinerea, Monilinia fructigena* and *Penicilliu expansum*", *J. Plant Diseases and Protection*, vol. 101, (1), pp. 38-47, 1994.
Antonio, G., et al., "Identification of Killer Factor in the Yeast Genus *Metschnikowia*", *Biotechnology Letters*, vol. 13, (4), pp. 297-298, 1991.
Janisiewicz, W., "Postharvest Biological Control of Blue Mold on Apples", *Postharvest Pathology and Mycotoxins*, vol. 77, (3), pp. 481-485, 1987.
Janisiewicz, W., "Ecological Diversity, Niche Overlap, and Coexistence of Antagonists Used in Developing Mixtures for Biocontrol of Postharvest Diseases of apples", *Biological Control*, vol. 86, (5), pp. 473-479, 1996.
Jijakli, N.H., et al., "Biological Control of Postharvest *Botrytis cinerea* and *Penicillium* on Apples", *IOBC/WPRS Bulletin*, pp. 106-111, 1993.
Jijalki, M.H., et al., "Biological Control of *Botrytis cinerea* and *Penicillium* sp. On Post-Harvest Apples by Two Antagonistic Yeasts", *Med. Fac. Landbouww* Univ. Gent, vol. 58/3b, pp. 1349-1358, 1993.
Leibinger, W., et al., "Control of Postharvest Pathogens and Colonization of the Apple Surface by Antagonistic Microorganisms in the Field", *Biological Control*, vol. 87, (11), pp. 1103-1110, 1997.
Piano, S., et al., "Biocontrol capability of *Metschnikowia pulcherrima* against *Botrytis* postharvest rot of apple", *Postharvest Biology and Tech.*, vol. 11, pp. 131-140, 1997.
Piano, S., et al., "Biological Control of Postharvest Diseases of Apple", *Ministry of Univeristy and Research*, pp. 77-83.
Spadaro, D., et al., "Mechanisms of Action and Efficacy of Four Isolates of the Yeast *Metschnikowia pulcherrima* Active Against Postharvest Pathogens on Apples", *Postharvest Biology and Technology*, vol. 24, pp. 123-134, 2002.

* cited by examiner

*Primary Examiner*—Irene Marx
(74) *Attorney, Agent, or Firm*—John D. Fado; Evelyn M. Rabin (57) ABSTRACT

Strains of *Metschnikowia* species, in particular *Metschnikowia pulcherrima*, have been isolated from apple and shown to have antagonistic activity against *Penicillium expansum*, the causative agent of blue mold on apples. A unique feature of the strains is demonstrated activity at cold storage temperatures. The present invention is thus drawn to novel *Metschnikowia* isolates which are effective biological control agents against blue mold and to biocontrol compositions which include at least one of the isolates.

6 Claims, 8 Drawing Sheets

*M.p.* growth in NYDB at 1 C

*M.p.* growth in NYDB at 0 C

BIOLOGICAL CONTROL OF POSTHARVEST DECAY OF FRUIT USING STRAINS OF *METSCHNIKOWIA* SPECIES

FIELD OF THE INVENTION

The present invention relates to the biological control of postharvest diseases in fruit. More particularly, the invention relates to the biological control of blue mold, a cause of postharvest decay in fruits, using strains of *Metschnikowia* species.

DESCRIPTION OF THE RELEVANT ART

Postharvest diseases of fruits cause significant losses in the fruit industry worldwide. Fungicides have been the major means for treating fruits and vegetables for the prevention of postharvest disease, however, they are often only marginally effective and are often considered hazardous both to humans and the environment.

Biological control of postharvest diseases of fruits with antagonistic microorganisms has emerged as an effective alternative to fungicides. A saprophytic strain of *Pseudomonas syringae* (BioSave 110™, EcoScience Corp., Orlando, Fla.) has been used commercially on pome fruits in the United States since 1996 (Janisiewicz and Marchi. 1992. *Plant Dis*. vol. 78, pp. 466–470; Stack, J. P. 1998. Invited Papers, Abstracts-1, $7^{th}$ International Congress of Plant Pathology, Edinburgh, Scotland, BSPP, London). Although these pioneering products are effective, they have limitations with respect to spectrum of activity and efficacy under various environmental conditions and on various fruits. To address those limitations, new biocontrol approaches are being developed and include applying mixtures of antagonists (Janisiewicz, W. J. 1996. *Phytopathology*. vol. 86, pp. 473–479; Janisiewicz and Bors. 1995. *Appl. Environ. Microbiol*. vol. 61, pp. 3261–3267) and combining antagonists with non-fungicidal methods such as heat treatment (Conway et al. 1999. *HortScience*. vol. 34, pp. 700–704), cultural methods (Roberts, R. G. 1994. *HortScience. vol*. 29, pp. 758–762; Sugar et al. 1994. *Plant Dis*. vol. 78, pp. 791–795), and substances that are generally regarded as safe (Conway et al., supra; El-Ghaouth et al. 2000. *Posth. Biol. Technol*. vol. 19, pp. 103–110; Janisiewicz et al. 1998. *HortScience. vol*. 33, pp. 105–109; Wisniewski et al. 1995. *Plant Pathol. vol*. 44, pp. 116–124). Biological control also can be improved by more rigorous selection of the antagonists, and physiological or genetic improvement of the antagonist strains to meet specific niche requirements and enhance biocontrol traits (Bassett and Janisiewicz. 2001. In: Proceedings of $76^{th}$ Cumberland-Shenandoah Fruit Workers Conference, 16–17 Nov. 2000. Wincester, Va.; Teixido et al. 1998. *Phytopathology*. vol. 88, pp. 960–964; Teixido et al. 1998. *J. Appl. Microbiol*. vol. 84, pp. 192–200).

Since the first report on the occurrence on fruit of naturally-occurring antagonists against postharvest fruit decay caused by *P. expansum* (Janisiewicz. W. J. 1987. *Phytopathology*. vol. 77, pp. 481–485), many effective bacterial (Bryk et al. 1998. *BioControl*. vol. 43, pp. 97–106; Costa et al. 2000. *J. Appl. Microbiol*. vol. 89, pp. 793–800; Dock et al. 1998. *J. Food Protect*. vol. 61, pp. 1661–1665; Janisiewicz and Marchi. 1992. *Plant Dis*. vol. 76, pp. 555–560; Mari et al. 1996. *Biological Control*. vol. 7, pp. 30–37; Sobiczewski and Bryk. 1996. Polesny et al. eds. *International Conference on Integrated Fruit Production*. Cedzyna, IOBC. vol. 19, pp. 344–345; Sobiczewski et al. 1996. *J. Fruit and Ornamental Plant Res*. vol. 6, pp. 35–45) and yeast (Chand-Goyal and Spotts. 1996. *Postharvest. Biol. Technol*. vol. 7, pp. 51–64; Chand-Goyal and Spotts. 1997. *Biological Control*. vol. 10, pp. 199–206; Galcone and Mendgen. 1994. *Zeitschrift für Pflanzenkrankheiten und Pflanzenschutz*. vol. 101, no. 1, pp. 38–47; Filonow et al. 1996. *Biological Control*. vol. 7, pp. 212–220; Ippolito et al. 2000. *Postharvest. Biol. Technol*. vol. 19, pp. 265–272; Janisiewicz et al. 1994. *Plant Dis*. vol. 78, pp. 466–470; Jijakil and Lepoivre. 1993. IOBC/WPRS Bulletin: *Biological Control of Foliar and Post-Harvest Diseases*. vol. 16, no. 11, pp. 106–110; Jijakli et al. 1993. *Med. Fac. Landbouww*. Univ. Gent. vol. 58, no. 3b, pp. 1349–1358; Leibinger et al. 1997. *Phytopathology*. vol. 87, pp. 1103–1110; McLaughlin et al. 1992. *Plant Dis*. vol. 76, pp. 470–473; McLaughlin et al. 1990. *Phytopathology*. vol. 80, pp. 456–461; Migheli et al. 1997. *Med. Fac. Landbouww*. Univ. Gent. vol. 62, pp. 1065–1070; Piano et al. 1998. In: *Proc Joint Workshop*, COAST 914–915, Bologna, Italy, Oct. 9–11, 1997, pp. 121–126; Piano et al. 1997. *Postharvest. Biol. Technol*. vol. 11, pp. 131–140; Roberts, R. G. 1990. *Phytopathology*. vol. 80, pp. 526–530; Schiewe and Mendgen. 1992. *J. Phytopathology*. vol. 134, pp. 229–237; Sugar et al., supra; Usall et al. 2000. *Int. J. Food Microbiol*. vol. 58, pp. 83–92; Vinas et al. 1998. In. *J. Food Microbiol. vol*. 40, pp. 9–16; Wisniewski et al. 1988. In: $46^{th}$ *Annual Meeting of the Electron Microscopy Society of America*, Bailey, G. E., ed. San Francisco, San Francisco Press, Inc., pp. 290–291) antagonists have been isolated from pome fruits, and the most effective were found among the resident microflora of apples. From 13 yeast species reported to be residents of apple (Davenport, R. R. 1976. In: *Microbiology of Aerial Plant Surfaces*, Dickinson and Preece, eds. Academic Press, London, pp. 325–374), seven (Chand-Goyal and Spotts, 1996, supra; Chand-Goyal, 1997, supra; Falcone and Mendgen, supra; Ippolito et al., supra; Janisiewicz et al., 1994, supra; Leibinger et al., supra; Lima et al. 1998. *Biocont. Sci. Technol*. vol. 8, pp. 257–267; McLaughlin et al. 1992, supra; Roberts, R. G., supra; Wisniewski et al. 1988, supra) had strong antagonistic activity against postharvest decays of pome fruits.

*Metschnikowia pulcherrima* (*M. pulcherrima*) has been recognized as one of the thirteen resident species on cider apple trees (Davenport, R. R., supra). It has frequently been isolated from all floral parts and from buds of apple (Davenport, R. R., supra). It has also been one of the most frequently isolated microorganisms from wounded apple tissue in an orchard (Janisiewicz, W. J., 1996, supra). It is a dominant species on mature grapes (Davenport, R. R., supra) and on the bloom of icewine grapes (Chamberline et al. 1997. *Food Res. Inter*. vol 30, pp. 435–439). It has been reported to control *Botrytis cinerea* on apples (Migheli et al. supra; Ippolito and Nigro. 2000. *Crop Protection*. vol. 19, pp. 715–723) and postharvest decay of peach and table grapes (DeCurtis et al. 1996. *Ann. Microbiol. Enzymol*. vol. 46, pp. 45–55).

SUMMARY OF THE INVENTION

I have discovered that strains of *Metschnikowia* species, in particular, *M. pulcherrima*, are highly effective antagonists against *Penicillium expansum* (*P. expansum*), the causative agent of blue mold, a postharvest disease of fruits and that the antagonists are effective at cold storage temperatures. In accordance with this discovery, it is an object of the invention to provide novel biological control agents which are safe and highly effective for the control of blue mold on fruits susceptible to the disease. In particular, these agents are isolated strains of *Metschnikowia* species which are effective for inhibiting the occurrence of blue mold on fruits.

It is also an object of the invention to provide a composition comprising at least one isolate of *Metschnikowia* species which is effective for controlling blue mold on fruits and an acceptable carrier.

It is a further object of the invention to provide a method for the biological control of blue mold comprising treating fruits susceptible to blue mold with the novel biocontrol agent.

Other objects and advantages will become readily apparent from the following description.

DETAILED DESCRIPTION OF THE INVENTION

*Metschnikowia* species may be obtained from the fruit, from all floral parts and from buds of apple trees (Davenport, R. R., supra). It may also be present in wounded apple tissue in an orchard (Janisiewicz, W. J., 1996, supra). An effective method for isolating the microorganism from wounded fruit is described in Example 1.

Isolates may be identified by the following identifying physical characteristics: cream to pink butyrous colonies producing pulcherrimin stains which can be enhanced by growth on medium with ferric ammonium citrate.

The microorganisms are grown under aerobic conditions at any temperature effective for the growth of the organism, e.g. from about 0° C. to about 37° C. Effective culture media are commercially available and include YM, malt agar, NYDA and NYDB. Preferred is YM or malt agar. The pH of the media is about neutral, i.e. about 6.7 to about 7.2, but the strains can grow in apple juice of pH about 3.7. The incubation time necessary for the organisms to reach a stationary growth phase varies with temperature for various isolates and may be readily determined by routine experimentation by one of skill in the art.

Isolates may be grown in any conventional shake flask for small batches or in a fermentation tank with agitation and aeration for large batches. Following incubation, the microorganisms are harvested by conventional sedimentation, e.g. centrifugation or filtration. Cultures may be refrigerated at 4° C. until used.

The microorganisms may be used for the control of blue mold on any fruits susceptible to the disease, including but not limited to, pome fruits such as apples and pears, and cherries. The organisms are applied to the fruits as a composition comprising one or more isolates in combination with any acceptable carrier. Carriers are commercially available and must be safe for human consumption. Materials such as dusts or suspensions with water or natural plant oils, such as corn oil and cottonseed oil, are useful. The organisms may also be applied in suspension with liquid culture medium. The compositions may also include conventional additives such as surfactants and wetting agents to enhance the effectiveness of the organisms. As an integrated approach, the organisms may also be used in combination with very low concentrations of fungicide.

Effective concentrations are any which inhibit the development of the targeted pathogen, i.e. *P. expansum*, when applied to the fruit. Exemplary concentrations range from about $2.5 \times 10^6$ CFU/ml to about $6 \times 10^7$ CFU/ml, preferably about $2 \times 10^7$ CFU/ml (CFU represents "colony forming units"). The composition may contain one or a mixture of the microorganisms.

The biocontrol composition may be applied to fruit using conventional methods such as dipping, spraying or brushing. In addition, they may be incorporated into waxes, wraps or other protective coatings used in processing the fruit.

The fruit may be treated anytime before or after harvest, typically after harvest and before storage and/or shipment. A particularly important aspect of the invention is the ability of the microorganisms to grow at the low temperatures generally used for cold storage of harvested pome fruits, i.e. about 0° C. to about 1° C.

The biocontrol agent of the invention encompasses *Metschnikowia* species sufficiently antagonistic to *P. exapansum* to inhibit its growth on harvested pome fruits. In order to ensure availability to the public of effective strains, cultures of isolated strains have been deposited under the provisions of the Budapest Treaty on May 14, 2002 with the U.S.D.A. Agricultural Research Service Patent Culture Collection (National Center for Agricultural Utilization Research, 1815 N. University Street, Peoria, Ill., 61604). The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action. Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

These strains were obtained from apples taken in different years from an unmanaged orchard at the Appalachian Fruit Research Station, Kearneysville, W. Va. and are identified as T5-A2, designated NRRL Number Y-30590; T4-A2, designated NRRL Number Y-30589; ST1-D10, designated NRRL Number Y-30585; ST2-A10, designated NRRL Number Y-30586; ST3-E1, designated NRRL Number Y-30587; ST3-E13, designated NRRL Number Y-30588; FMB-24H-2, designated NRRL Number Y-30591: and FMB-140H-7A, designated NRRL Number Y-30592. They were identified as *M. pulcherrima* strains by traditional methods at the Centraalbureau Voor Schimmelcultures, Delft, The Netherlands. There is significant diversity among the strains in phenotypic and functional characteristics. This diversity is supported by results of analysis of nucleotide sequences from the species-variable D1/D2 domain of 26S ribosomal DNA (rDNA) where some divergence among the isolates was detected. All the strains selected, however, exhibit the unique characteristics which are necessary for effective antagonistic activity against *P. expansum*. In particular, the ability to function effectively at cold-storage temperatures is a unique and important characteristic for use on fruits which spend a considerable amount of time at those temperatures.

Isolated strains of an antagonist species may be tested for effectiveness in controlling fruit decay and for other characteristics useful for evaluating commercial potential, then selected for use according to test results. Useful criteria for decay control on apple include biological control potential with respect to efficacy and spectrum of activity, the ability to colonize fruit surfaces under various conditions, utilization of substrates occurring in fruits, growth at cold storage temperatures and at 37° C. (human body temperature), and compatibility with antioxidants which may be used for control of various physiological disorders, e.g. diphenylamine (DPA) used for the control of superficial scald. Additional criteria may include resistance to environmental stress in the orchard, if biocontrol agents are to be applied before harvest (Benbow and Sugar. 1999. *Plant Dis.* vol. 83, pp. 839–844; Ippolito and Nigro, supra; Leibinger et al., supra; Teixido et al. 1999. *Int. J. Food Microbiol.* vol. 50, pp. 203–210; Teixido et al., 1998, *J. Appl. Microbiol.*, supra), and pathogenicity of the antagonists to fruits, since strains of some antagonists, such as *Aureobasidum pullulans*, have good biocontrol potential but can cause minor decay on some fruits (Chand-Goyal, 1996, supra; Dugan and Roberts. 1994. *Phytopathology.* vol. 84, pp. 1031–1036; Rist and Rosenberger. 1995. *Plant Dis.* vol. 79, p. 425).

Studies were thus carried out to compare the effectiveness and usefulness of *M. pulcherrima* strains isolated at different times from an unmanaged orchard in controlling blue mold of apple. Eight isolates were obtained from apples as described in Example 1, and experiments were carried out which tested the biocontrol activity of the isolates (see Example 3).

Figure 1:
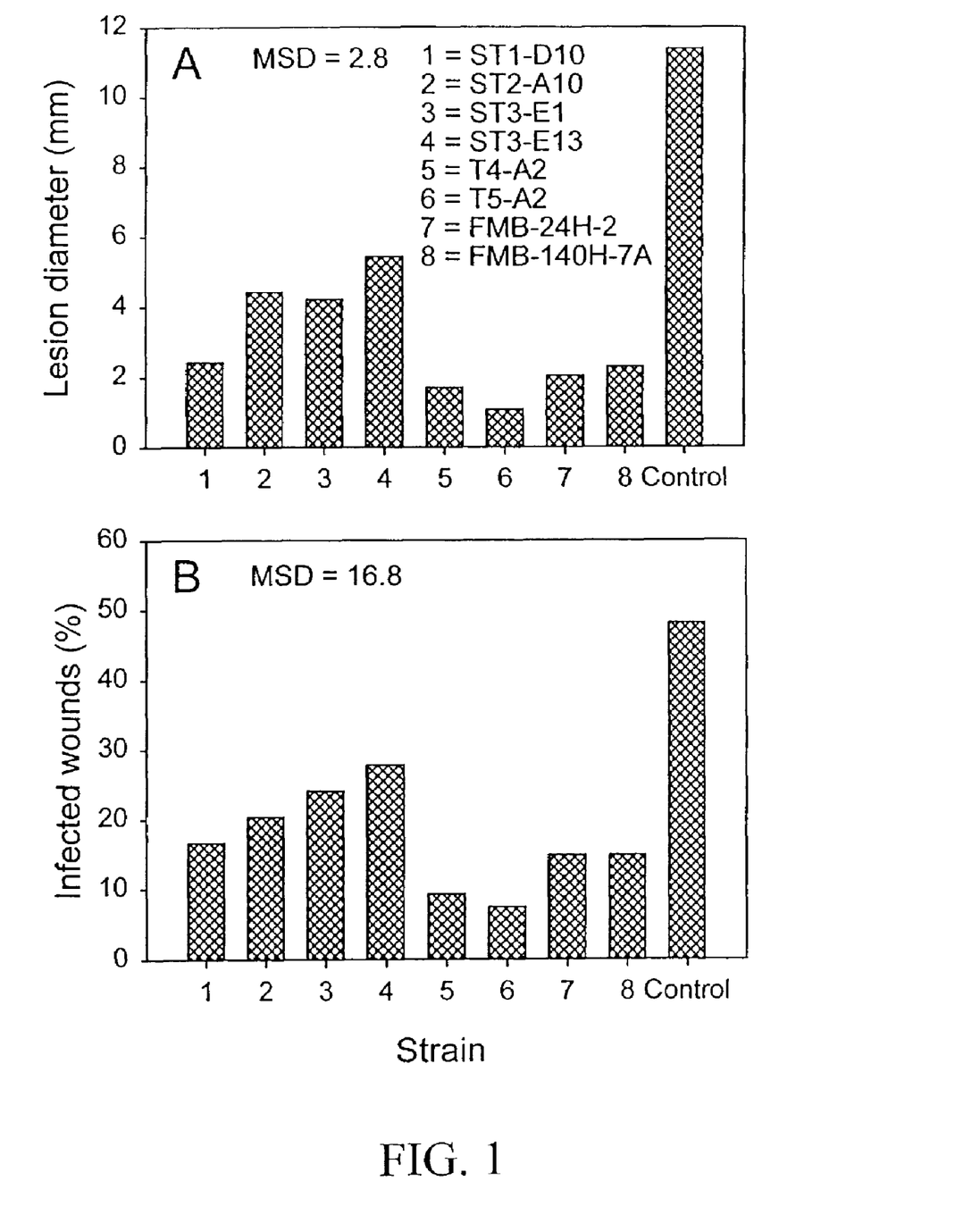
FIG. 1 shows the control of blue mold on mature (stored for eight months at 1° C. before application of treatments) 'Golden Delicious' apples inoculated with *P. expansum* alone (control) or in combination with the individual strains of *M. pulcherrima* ($1.6 \times 10^7$ CFU/ml) and stored for one month at 1° C. followed by 7 days at room temperature. Minimum significant difference (MSD) is for comparing treatments with strains of *M. pulcherrima*, the control treatment was not included in the statistical analysis.

In the first test, very mature apples which had been stored for 8 months were wound-inoculated with a mixture of the antagonist and the pathogen *P. expansum*, the causative agent of blue mold in apples (see Example 2). After inoculation, apples were stored for 1 month at 1° C., followed by storage at room temperature (RT) for 7 days. All strains reduced the severity and incidence of decay. Strain T5-A2 was the most effective in reducing severity of decay, and strains T5-A2 and T4-A2 were the most effective in reducing the incidence of decay. Results are shown in FIG. 1.

Figure 2:
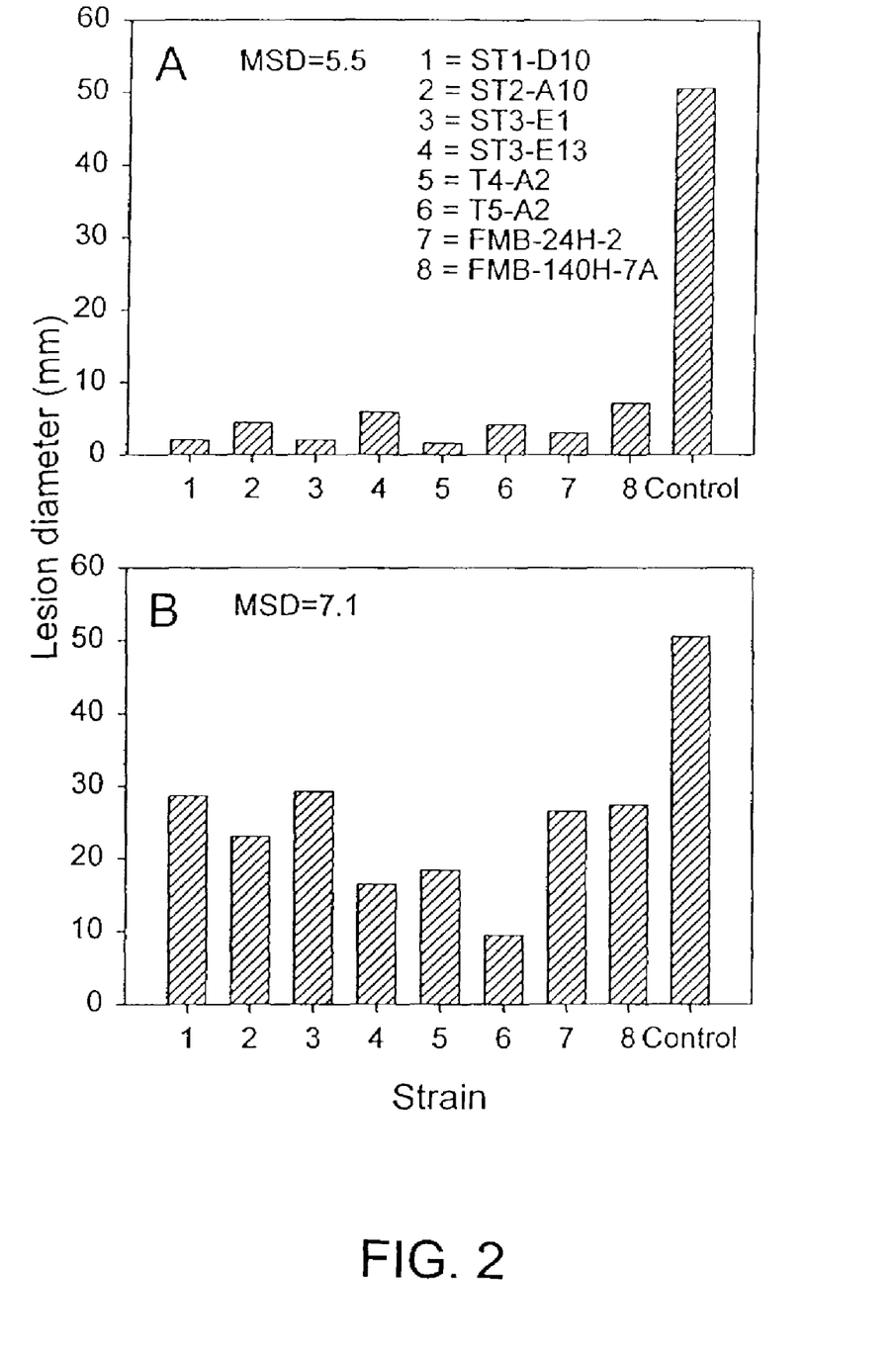
FIG. 2 shows the severity of blue mold decay on 'Golden Delicious' apples (stored for less than one month at 1° C. before application of treatments) inoculated with *P. expansum* alone (control) or in combination with the individual strains of *M. Pulcherrima* at $1.6 \times 10^7$ CFU/ml (A); and $1.6 \times 10^5$ CFU/ml (B) and stored for three months at 1° C. Minimum significant difference (MSD) is for comparing treatments with strains of *M. pulcherrima*, the control treatment was not included in the statistical analysis.
Figure 3:
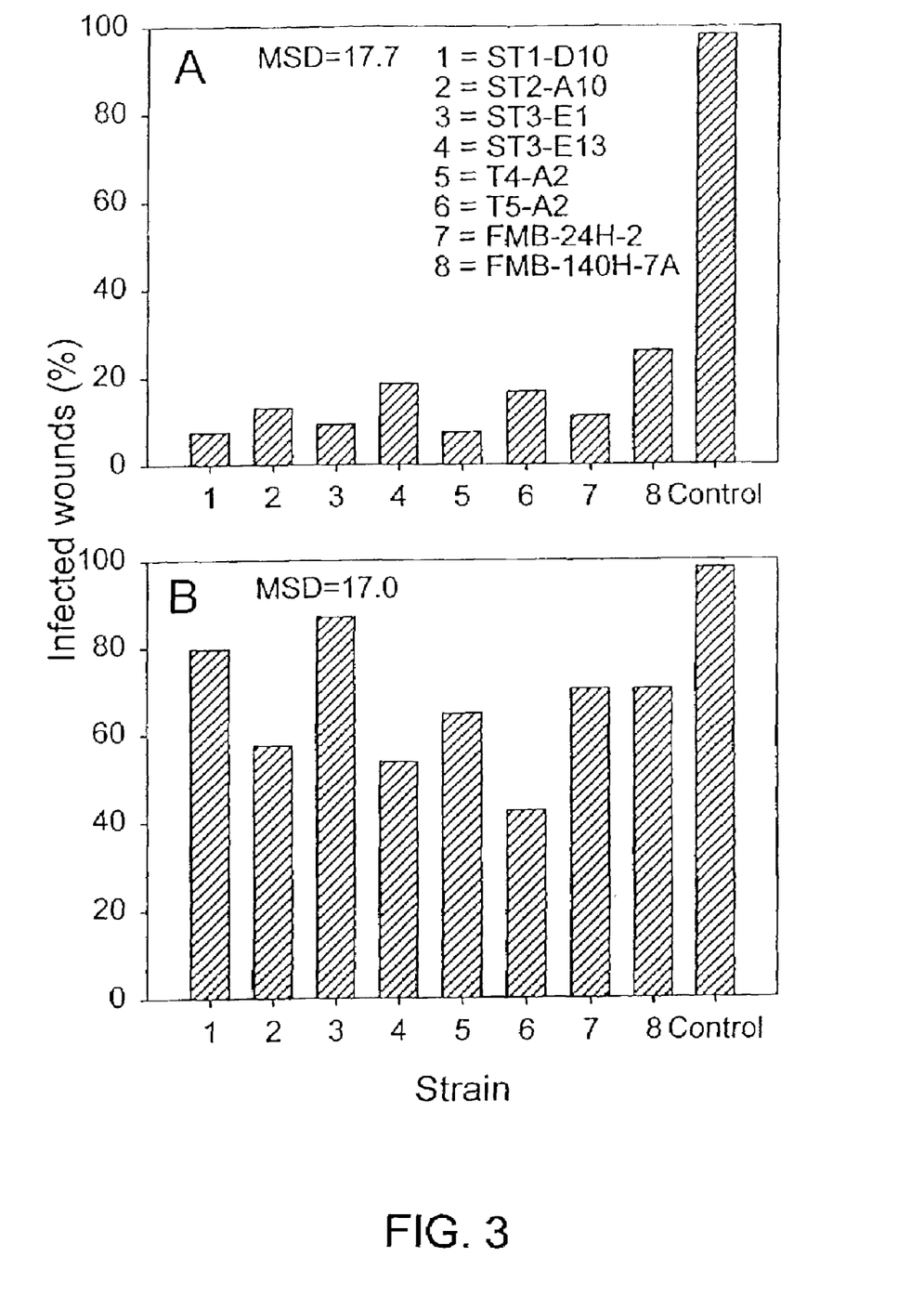
FIG. 3 shows the incidence of blue mold decay on 'Golden Delicious' apples inoculated with *P. expansum* alone (control) or in combination with the individual strains of *M. pulcherrima* at A) $1.6 \times 10^7$ CFU/ml; and B) $1.6 \times 10^5$ CFU/ml and stored for three months at 1° C. The control treatment was not included in the statistical analysis.

In a second test, apples were wound-inoculated one month after harvest. The apples were inoculated as described above with two additional 1:10 dilution (i.e. 1:100) of original antagonist concentration included. Approximately 1 hour after inoculation, apples were stored at 0.5° C. for 3 months. Little decay developed at the highest antagonist concentration, and there were no significant differences among antagonist strains, with the exception of strain FMB-140H-7A which had significantly higher severity and incidence of decay (FIGS. 2 and 3). On fruit protected with antagonist diluted a hundred-fold, strain T5-A2 was the most effective in reducing the severity and incidence of decay (FIGS. 2 and 3). The next most effective strains in reducing severity of decay were ST3-E13, T4-A2 and ST2-A10. In reducing the incidence of decay, the next most effective was ST3-E13, followed by ST2-A10, then T4-A2.

Figure 4:
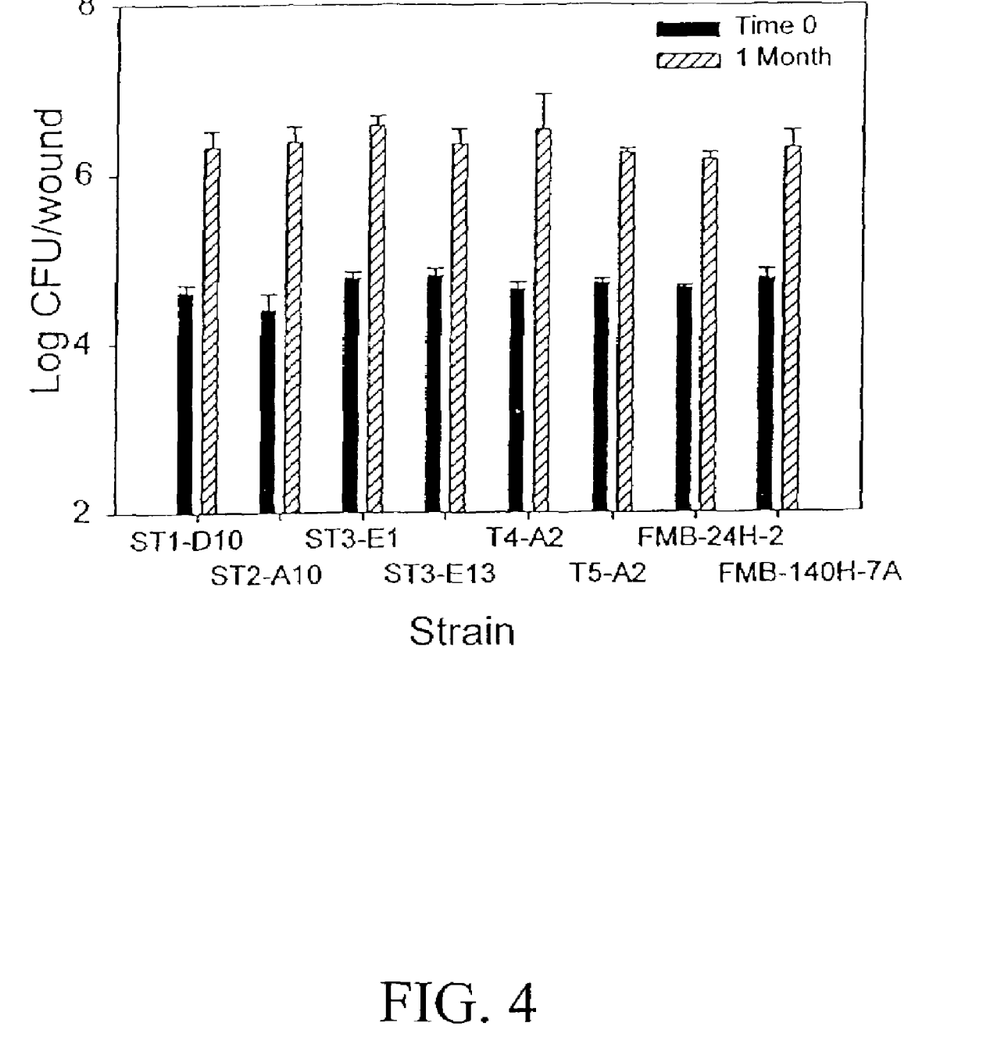
FIG. 4 shows populations of *M. pulcherrima* strains in wounds of 'Golden Delicious' apple at the time of inoculation (time 0) and after one month storage at 1° C. To determine population sizes in the wounds, the wounded area was removed with a cork borer, extracted in water using a Stomacher blender, dilution-plated on NYDA medium, and the yeast colonies were counted after incubation for 48 hr at 26° C. Bars indicate ±SD.

Tests were also conducted to determine growth capability of the various-strains on apple. Fruit were inoculated as described in Example 4. All eight strains grew well in apple wounds at 1° C. During a one-month period, populations increased approximately two log units for all strains (FIG. 4).

Figure 5:
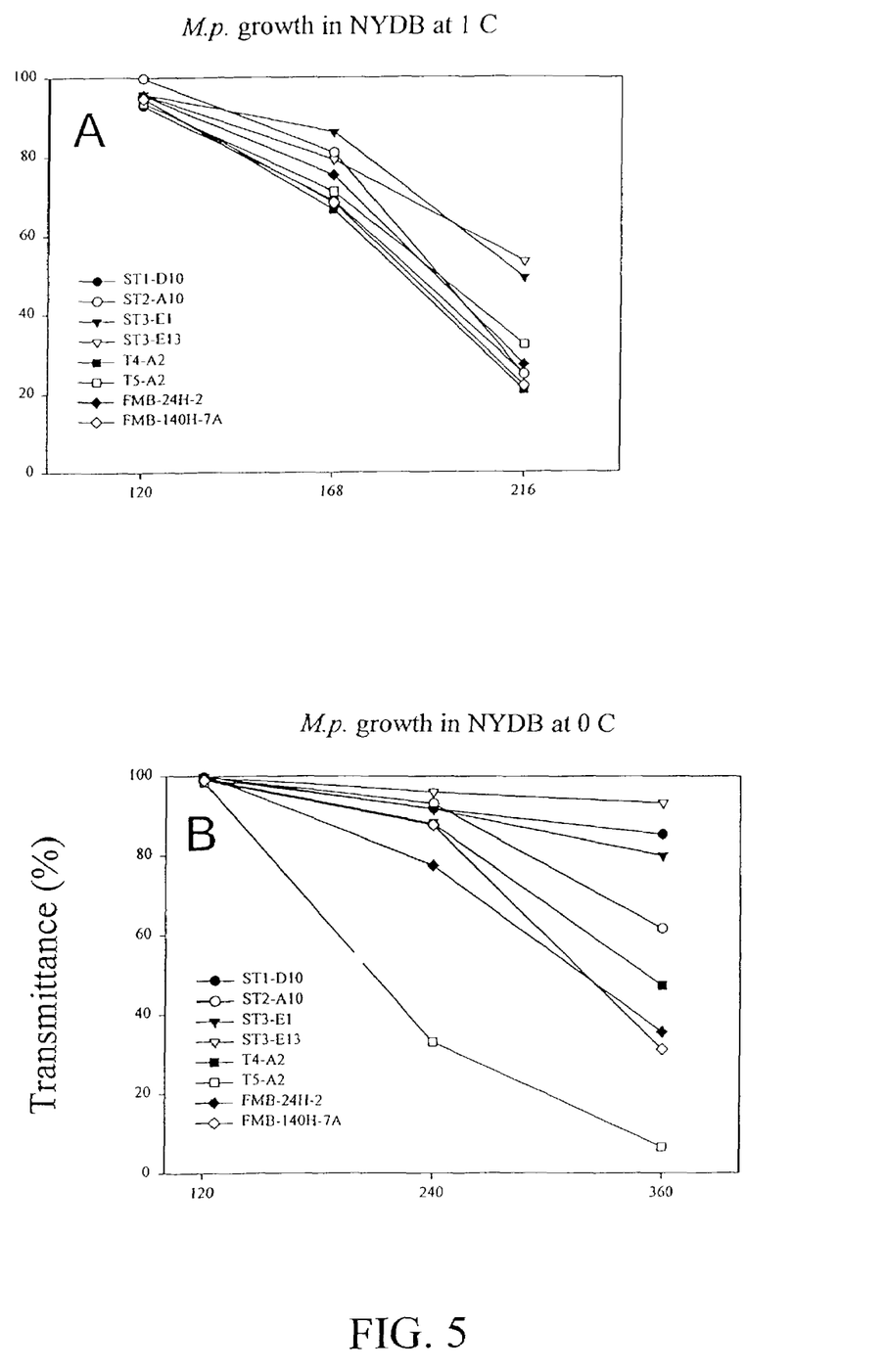
FIG. 5 shows the growth of the eight strains of *M. pulcherrima* in NYDB medium at A) 1° C.; B) 1° C.; and C) 37° C.

Experiments for phenotypic characterization and differentiation of the isolates were carried out as described in Example 5. All strains grew in nutrient yeast dextrose broth (NYDB) at 1° C. (FIG. 5). Two strains, ST3-E1 and ST3-E13, grew distinctively slower, and after 216 hr their growth was at least 18% Transmittance (% Transmittance represents the turbidity of the sample) less than the other strains. At 0° C. there was greater separation between strains, with strains ST3-E1, ST3-E13 and ST1-D10 growing the slowest and strain T5-A2 outgrowing all other strains by more than 25% Transmittance after 360 hr. None of the eight strains grew in NYDB medium at 37° C. (FIG. 5). After moving the flasks from 37° C. to 26° C., five strains, ST2-A10, ST3-E1, ST3-E13, T4-A2 and T5-A2 resumed growth and reached turbidity below 10% Transmittance after an additional 72 hr incubation. No subsequent growth occurred in flasks with strains ST1-D10, FMB-24H-2 and FMB140H-7A (data not shown).

Figure 6:
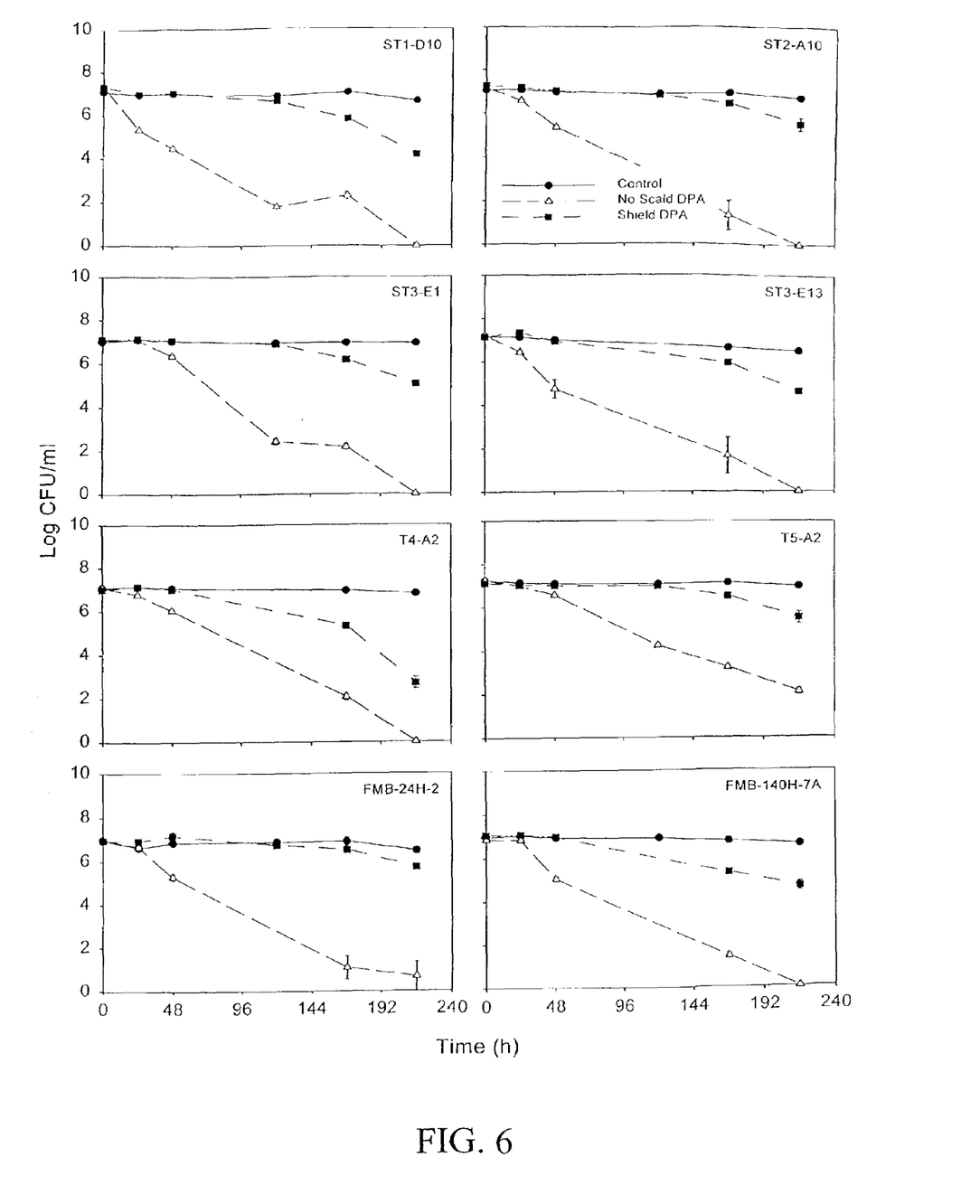
FIG. 6 shows the survival of the eight strains of *M. pulcherrima* in water (control) or aqueous suspensions of two commercial products No-Scald DPA or Shield DPA. Samples were taken from the flasks at time intervals, dilution-plated on NYDA medium, and colonies were counted after 48 hr incubation at 26° C. The concentration of the active ingredient diphenylamine (DPA) in the suspensions was at the commercially recommended rate of 0.2% (2000 ppm). Bars indicate ±SD.

There were significant differences in the tolerance of the eight *M. pulcherrima* strains to two different commercial formulations of the antioxidant diphenylamine (DPA)(Example 5). Results are shown in FIG. 6. Populations of all strains declined greatly in No-Scald DPA and were not recovered after 216 hr, with strain T5-A2 having an almost two log greater population than FMB-24H-2. Shield DPA had a much less negative effect on the survival of the yeasts. The populations started to decline noticeably after five days and generally did not decline more than two log units after nine days. The only exception was strain T4-A2, which declined more than four log units by the end of the experiment.

None of the eight *M. pulcherrima* strains produced killer toxins and did not inhibit the growth of the indicator strain *S. cerevisiae* (NCYC 1006) in the culture filtrate agar diffusion test or the cross streak test on nutrient yeast dextrose agar (NYDA) plates (see Example 5).

All strains required biotin for normal growth (Table 1). Strain ST2-A10 had limited growth on folic acid and riboflavin, and strain ST3-E1 had very limited growth in media without vitamins. Growth with a mixture of vitamins was generally similar to growth with biotin alone except with strain ST1-D10 where % Transmittance in the mixture was almost half of that with the biotin.

Figure 7:
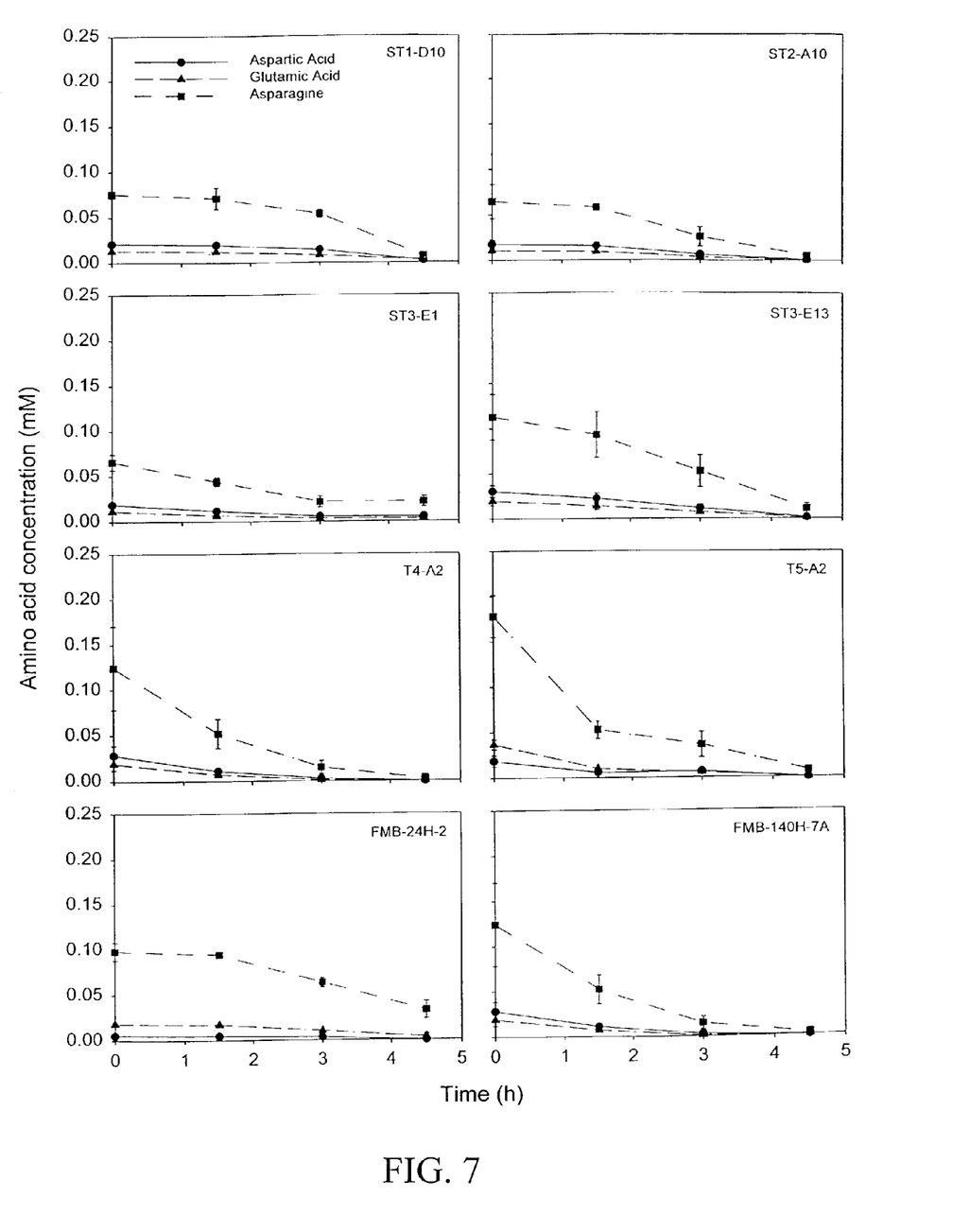
FIG. 7 shows the depletion of amino acids from 5% apple juice by various strains of *M. pulcherrima* at 26° C. *M. pulcherrima* strains were suspended in diluted apple juice, placed in wells of plastic tissue culture plates and incubated at 26° C. until the indicated sampling time. Samples were filtered to remove the yeasts, and the filtrate was analyzed by HPLC. Bars indicate ±SD.

Amino acid utilization was also tested (see Example 6). The three main amino acids in apple juice, asparagine, aspartic acid and glutamic acid, were utilized by all strains. Asparagine, aspartic acid, and glutamic acid concentrations of juice at time 0 were 0.161 mM, 0.042 mM and 0.028 mM, respectively. Amino acid concentrations at time 0 (immediately after mixing juice with the antagonists) was not modified by strain T5-A2 but was reduced by all other strains (FIG. 7). Amino acids were completely depleted by the strains except ST3-E1 and FMB-24H-2 within 4.5 hr of mixing.

mature fruit. These two strains differed in characteristics important for implementation of biocontrol. For example, strain T5-A2 grew exceptionally well and had the strongest growth at 0° C., a particularly useful characteristic for application to apples and pears which are typically stored at 0° C. or even lower temperatures in case of pears.

All eight strains grew well in NYDB medium at 1° C. and increased in population by approximately two log units in apple wounds during one month storage at 1° C. This is a good indication of their commercial potential for biocontrol of postharvest decays of apple that are stored at this temperature. Lack of growth at 37° C., the human body temperature, by all strains may reduce the number of tests necessary for registration of the antagonists by the Environmental Protection Agency (EPA). The three strains that were killed by prolonged exposure to 37° C. are not suitable for any treatment that combines an antagonist with exposure to hot air (4 days at 38° C.), a treatment which can significantly improve decay control on apples (Conway, supra).

An increase in population by approximately two log units in apple wounds, as well as rapid removal of the amino acids from apple juice by all strains, confirmed that these antagonists are excellent colonizers of apple wounds and can thrive on apple as a substrate. However, under the conditions of the experiments, these characteristics did not differentiate strains well. Additional tests, those that reflect the kinetics of growth in apple wounds, and the utilization of amino acids under different conditions could indicate potential differences among the strains.

Biotin was required for efficient growth by all strains. If the availability of biotin is a limiting factor in growth of the yeast in fruit wounds, the addition of biotin to a biocontrol composition may significantly increase populations of the antagonist, thereby enhancing biocontrol activity. It may also be possible to develop a mixture of antagonists comprising a strain of *M. pulcherrima* and a yeast capable of

TABLE 1

Growth of *M. pulcherrima* strains in MS medium containing individual vitamins and their mixture.

| Vitamin | Strain | | | | | | | |
|---|---|---|---|---|---|---|---|---|
| | ST1-D10 | ST2-A10 | ST3-E1 | ST3-E13 | T4-A2 | T5-A2 | FMB-24H-2 | FMB-140H-7A |
| | % Transmittance after 22 Hours* | | | | | | | |
| p-Aminobenzoic Acid | 99.7 | 99.2 | 93.2 | 96.9 | 99.9 | 99.0 | 98.3 | 99.6 |
| Biotin | 18.6 | 10.2 | 7.9 | 10.8 | 11.8 | 8.7 | 11.2 | 13.0 |
| Folic Acid | 99.7 | 89.6 | 93.6 | 98.7 | 99.9 | 99.9 | 99.0 | 99.7 |
| Myo-inositol | 99.8 | 93.5 | 95.2 | 97.8 | 99.6 | 99.6 | 99.1 | 99.5 |
| Nicotinic Acid | 99.2 | 98.3 | 95.2 | 98.8 | 99.9 | 99.5 | 99.1 | 99.8 |
| d-Pantothenate | 99.5 | 98.8 | 95.0 | 98.4 | 99.9 | 99.3 | 98.6 | 99.5 |
| Pyridoxine HCl | 99.4 | 96.4 | 94.9 | 96.8 | 99.9 | 98.2 | 98.9 | 99.0 |
| Riboflavin | 99.7 | 78.5 | 94.2 | 98.8 | 99.8 | 99.5 | 99.2 | 99.3 |
| Thiamin HCl | 99.8 | 93.8 | 93.7 | 98.5 | 99.7 | 98.4 | 97.8 | 99.8 |
| Mixture | 9.5 | 8.7 | 8.2 | 8.8 | 10.6 | 9.7 | 11.0 | 12.3 |
| None | 99.6 | ND | 94.1 | 97.5 | 99.8 | 98.6 | 98.2 | 99.5 |

*±2 hours
Addition of vitamin mixture and yeasts to MS medium reduced transmittance by <1% for all samples at 0 hr.

The eight strains varied in biological control of blue mold under conditions most favorable for decay development on mature 'Golden Delicious' apple. Strains T5-A2 and T4-A2 were the most effective in reducing decay. Strain T5-A2 was also most effective in the second biocontrol test on less producing biotin to enhance *M. pulcherrima* population growth, thereby improving biocontrol activity.

Inert ingredients in No-Scald DPA were most likely responsible for the rapid population decline of all eight strains because there was less decline if the yeast strains were exposed to Shield DPA at the same active ingredient concentration. Similar effects were obtained in tests with *P. expansum* conidia, where the ability of the conidia to germinate declined more rapidly after exposure to No-Scald DPA than to Shield DPA (Janisiewicz, unpublished results). A few strains, including T5-A2, were very resistant to DPA and can be considered for biological control in packing houses in the Central and Eastern United States where it is common practice to keep DPA treatment suspensions, in which the antagonist will be applied, for up to one week before changing.

The following examples are intended to further illustrate the invention and not to limit the scope of the invention as defined by the claims.

EXAMPLES

Example 1

Isolation of Microorganisms

Microorganisms were isolated from wounds of artificially wounded 'Golden Delicious' or 'Red Delicious' (*Malus domestica*, Burk.) apples from 6 to 10 year-old unmanaged apple orchard trees planted to 'Golden Delicious', 'Red Delicious', 'Empire', 'Stayman' and 'York' at the Appalachian Fruit Research Station in Kearneysville, W. Va. as described by (Janisiewicz, W. J., 1996, supra) with a few modifications. Apples were collected from the orchard in three different years. Briefly, 'Golden Delicious' apples were wounded by removing the skin in an area of approximately 3 cm$^2$ and 2 mm deep at weekly intervals starting five weeks before harvest in the first year, and only once 4 weeks before harvest in the second year. In the third year, 'Red Delicious' apples were wounded one week before harvest. The wounded areas on fruits were removed for isolation of microorganisms with a cork borer (1 cm diameter×1 cm deep) one week after each wounding in the first year; one, two, three and four weeks after wounding in the second year; and one week after wounding in the third year. In the first and second years, samples were ground with mortar and pestle in phosphate buffer and dilution plated on NYDA medium and, after incubation, colonies were isolated and purified as described by (Janisiewicz, W. J., 1996, supra). In the third year, the samples were ground in 4.5 ml of water and the resulting slurry was added to 200 ml of 10% apple juice in 500 ml Erlenmeyer flasks, and shaken at 150 rpm at 26° C. At 42 and 66 hr, 2 ml of the culture was transferred to fresh 10% apple juice which was used for subsequent sampling. Samples for dilution plating were taken after 0, 24, 42, 66 and 140 hrs, and after incubation of the plates, colonies were purified as described by (Janisiewicz, W. J., 1996, supra).

Example 2

Pathogen and Antagonists

The pathogen used was a very aggressive isolate of *P. expansum* (MD-8) from a collection which was previously isolated from a decayed apple in storage. It was maintained on potato-dextrose-agar (PDA), and continued virulence was assured by periodic transfers through apple. A conidial suspension (5×10$^4$ conidia/ml) was used for fruit inoculations as described by (Janisiewicz and Marchi, supra).

Suspensions of the *M. pulcherrima* strains for fruit inoculation and nutrient utilization tests were prepared as described by (Janisiewicz and Marchi, supra). Briefly, the yeasts were grown in 50 ml of NYDB medium in 250 ml Erlenmeyer flasks on a rotary shaker at 150 rpm at 26° C. Following incubation for 24 hr, the cells were harvested by centrifugation at 7000 g$_n$ for 10 min, resuspended in water and adjusted to a concentration 1.6×10$^7$ CFU/ml with a spectrophotometer at 420 nm. For the second biocontrol experiment, additional concentration adjustments were performed by two ten-fold dilutions of the original concentrations.

Example 3

Antagonist Selection and Upscale Biocontrol Tests

The biocontrol potential of the isolated microorganisms against *P. expansum* was determined in primary and secondary screenings on 'Golden Delicious' apples (24). Eight yeast strains, which came from the three types of isolation procedures in three different years, and identified as *M. pulcherrima* by Centraalbureau Voor Schimmelcultures, Delft, the Netherlands, were selected for upscale biocontrol tests on 'Golden Delicious' apple. The selected yeasts included strains: T4-A2 and T5-A2 from the first-year isolation; ST1-D10, ST2-A10, ST3-E1 and ST3-E13 from the second-year isolation; and FMB-24H-2 and FMB-140H-7A from the third-year isolation.

In the first test, very mature apples stored for eight months in air storage at 1° C. were removed from storage, washed, dried, placed on fruit tray packs and equilibrated to room temperature overnight. The next day the fruit were wounded midway along the calyx-stem end axis with a standardized tool that had two six-penny nails (4 mm diameter) placed 2 cm apart and protruding 3 mm from a wooden block. Each wound was inoculated with 25 μl of a pathogen/antagonist mixture or the pathogen alone (control). The pathogen inoculum concentration was 5×10$^4$ conidia/ml, and the antagonist was applied at 1.6×10$^7$ CFU/ml. After inoculations, apples were placed in boxes with polyethylene liners and stored at 1° C. for one month. The fruit were then stored at room temperature for 7 days and evaluated for decay development. There were three replicates per treatment and nine apples per replicate. Apples were arranged in a completely randomized design.

In the second test, apples were used within one month after harvest. The fruit were inoculated as before and at an additional two 1:10 dilutions of the original antagonist concentration. Approximately 1 hr after inoculating the fruit, when the inoculation suspension was no longer visible in the wounds, fruit were placed in wooden crates in polyethylene liners and stored at 0.5° C. for 3 months.

Example 4

Population Dynamics on Apple

'Golden Delicious', apples were wounded as above and inoculated with 25 μl of approximately 1.6×10$^7$ CFU/ml of *M. pulcherrima* strains. The yeast strains were isolated from the wounds within 2 hr after application (time 0) and after 1 mo in storage at 1° C. followed by 5 days at 24° C. according to the procedure described by (Janisiewicz and Jeffers, supra). Wounded tissue was removed with a cork borer, extracted with water in a Stomacher blender (Seward Medical, London, England), plated on NYDA medium with a Spiroplater (Spiral Biotech, Bethesda, Md.), and colonies were enumerated with a Casaba II laser counter and the Ben 4.0 program (Spiral Biotech, supra) system.

Example 5

Physiological Characterization and Differentiation of M. Pulcherrima Isolates Physiological tests were conducted to characterize strains of *M. pulcherrima* taxonomically and to determine biocontrol usefulness of the strains. The growth potential on various carbon and nitrogen sources and the resulting relatedness of *M. pulcherrima* strains was determined with YT plates of the Biolog system (Biolog Inc, Hayward, Calif.) according to the recommended procedure. The plates were inoculated with the yeast suspensions made from cultures grown in NYDB medium overnight, which were washed twice in sterile distilled water before application to the plates. The data from the YT plates was analyzed with the MLCLUST program (Biolog, Inc., supra).

To determine growth of the strains at 0° C., 1° C. and 37° C., the yeasts were grown in NYDB medium overnight, and aqueous suspensions of the yeasts at ~$1.6 \times 10^7$ CFU/ml were prepared for each isolate as above. Then, 125 ml Erlenmeyer flasks, each containing 50 ml of NYDB medium, were inoculated with one ml of the yeast cell suspension and placed on a shaker at 150 rpm. Growth of the yeasts in the flasks was determined by measuring the turbidity of the cultures at 640 nm at time intervals over 168 h, 216 h and 360 h for flasks incubated at 37° C., 1° C. and 0° C., respectively. Due to the lack of growth after 168 h at 37° C., strain viability was determined by transferring the flasks to 26° C. and determining the growth after an additional 72 hr. The identity of the strains in flasks with growth was confirmed by microscopic and visual observation of the colonies that grew after streaking the cultures on plates with NYDA medium and incubating them at 26° C. for 72 hr.

The requirement of the yeast strains for vitamins was determined in minimum salt (MS) medium as described by Barnett et al. (Barnett et al. 1990. *Yeasts: Characteristics and identification*. Cambridge University Press, New York, p. 1002). Briefly, nine vitamins: p-aminobenzoic acid, biotin, folic acid, myo-inositol, nicotinic acid, pantothenate (Ca), pyridoxine HCl, riboflavin and thiamine HCl, individually or in combination were added to 50 ml of the MS medium in 125 ml Erlenmeyer flasks. The flasks were inoculated with 1 ml (75% Transmission at 420 nm) of aqueous suspensions of the *M. pulcherrima* strains and incubated on a shaker at 150 rpm at 26° C. Turbidity of the cultures at 420 nm was determined immediately after inoculation and after growth for 24 hr.

The eight *M. pulcherrima* strains were tested for production of the killer toxin using a sensitive strain of *Saccharomyces cerevisiae* (*S. cerevisiae*) NCYC 1006 (National Collection of Yeast Cultures, Norwich, UK) sensitive to the killer toxin (Farris et al. 1991. *Biotech. Lett. vol.* 13, pp. 297–298): Filter-sterilized supernatants of the eight yeast cultures grown in NYDB for seven days were evaluated by an agar diffusion test on NYDA plates. One cm diameter wells were made in the center of the agar plates using a cork borer, and 100 μl samples of the supernatent were placed in the wells. After 24 hr incubation at 4° C., the plates were seeded with the 24 hr-old culture of the indicator strain and incubated at RT. The plates were evaluated daily for zones of growth inhibition. There were three plates per treatment. In the second test, the *M. pulcherrima* strains and the indicator strain of *S. cerevisiae* were streaked perpendicularly across the NYDA plates without touching each other. The streaks with the eight isolates were made 24 hr before the streak with the indicator strain. The plates were evaluated daily for zones of growth inhibition. There were three plates per treatment.

To determine the tolerance of the yeast strains to diphenylamine (DPA), 100 ml of aqueous suspensions of the yeasts were prepared in 250 ml Erlenmeyer flasks at a concentration of approximately $1.6 \times 10^7$ CFU/ml as described above. One ml of concentrated stock solutions of two commercial DPA products, No-Scald DPA EC-283 (Elf Atochem America, Inc. Monrovia, Calif.) or Shield DPA (Pace Int. LP, Kirkland, Wash.), were added to the yeast suspension to make a final concentration of 0.2% active ingredient (equal to the commercially recommended concentration of 2000 ppm). The flasks were placed on a rotary shaker at 75 rpm at 26° C. The samples were collected at time intervals, dilution-plated on NYDA medium with a Spiroplater, and colonies were counted with the Casaba II laser couanter and BEN 4.0 program system after 48 hr incubation at 26C as described above. The experiment was repeated.

Example 6

Utilization of Amino Acids

To determine the ability of the yeast to utilize the major amino acids present in apple juice, tissue culture plastic plates (Costar, Corning Inc., Corning, N.Y.) were used as described by (Janisiewicz et al. 2000. *Phytopathology*. vol. 90, pp. 1196–1200). Briefly, 5% apple juice alone or with the yeast at a concentration $1.6 \times 10^6$ CFU/ml was dispensed into the wells of the tissue culture plates (1 ml/well). Suspensions containing an antagonist in apple juice were prepared by mixing 1:1 (v/v) of 10% apple juice and the water suspension of the antagonists. Then 1 ml of this suspension was placed in the wells and incubated at 26° C. There were three replicates (three wells) for each isolate at each sampling time. The amino acid concentration was determined with an HPLC using the procedure described by (Janisiewicz et al., 2000, supra).

Example 7

Statistical Analysis

The Waller-Duncan multiple-range test was performed for separation of means of lesion diameter and percentage of wounds infected on fruit treated with the eight strains of *M. pulcherrima* and *P. expansum* (SAS Institute. 1989. *SAS/SAT User's Guide*. Version 4, $4^{th}$ ed. SAS Institute, Inc., Cary, N.C.).

All references cited hereinabove are herein incorporated by reference in their entirety.

I claim:

1. A biologically pure culture of an antagonistic microorganism effective for the inhibition of infection of fruits by *Penicillium expansum* and for the inhibition of the severity of *Penicillium expansum*-induced disease on fruits, wherein the antagonistic microorganism is a *Metschnikowia* species selected from the group consisting of T5-A2 (NRRL Number Y-30590), T4-A2 (NRRL Number Y-30589), ST1-D10 (NRRL Number Y-30585), ST2-A10 (NRRL Number Y-30586), ST3-E1 (NRRL Number Y-30587), ST3-E13 (NRRL Number Y-30588), FMB-24H-2 (NRRL Number Y-30591) and FMB-140H-7A (NRRL Number Y-30592).

2. A biocontrol composition comprising an antagonistic microorganism effective for the inhibition of *Penicillium expansum* on fruits and an acceptable carrier, wherein the antagonistic microorganism is a *Metschnikowia* species selected from the group consisting of T5-A2 (NRRL Number Y-0590), T4-A2 (NRRL Number Y-30589), ST1-D10 (NRRL Number Y-30585), ST2-A10 (NRRL Number Y-30586), ST3-E1(NRRL Number Y-30587), ST3-E13 (NRRL Number Y-30588), FMB-24H-2 (NRRL Number Y-30591) and FMB-140H-7A (NRRL Number Y-30592).

3. The composition of claim 2, comprising a combination of at least two microorganisms selected from the group consisting of T5-A2 (NRRL Number Y-30590), T4-A2 (NRRL Number Y-30589), ST1-D10 (NRRL Number Y-30585), ST2-A10 (NRRL Number Y-30586), ST3-E1 (NRRL Number Y-30587), ST3-E13 (NRRL Number Y-30588), FMB-24H-2 (NRRL Number Y-30591) and FMB-140H-7A (NRRL Number Y-30592).

4. The composition of claim 2, wherein said antagonistic microorganism effective for the inhibition of *Penicillium expansum* on fruits is effective for said inhibition at cold storage temperatures.

5. The composition of claim 3, wherein said antagonistic microorganisms effective for the inhibition of *Penicillium expansum* on fruits are effective for said inhibition at cold storage temperatures.

6. The composition of any of one of claims 2–5, wherein said carrier is water, natural plant oils or dust.

* * * * *